(12) United States Patent
Hossack et al.

(10) Patent No.: US 6,338,716 B1
(45) Date of Patent: Jan. 15, 2002

(54) MEDICAL DIAGNOSTIC ULTRASONIC TRANSDUCER PROBE AND IMAGING SYSTEM FOR USE WITH A POSITION AND ORIENTATION SENSOR

(75) Inventors: John A. Hossack, Charlottesville, VA (US); Douglas J. Gallinat, San Jose, CA (US); Timothy E. Petersen, Mountain View, CA (US); Joseph J. Molinari, Redwood City, CA (US); Sean C. Little, Sunnyvale, CA (US)

(73) Assignee: Acuson Corporation, Mountain View, CA (US)

( * ) Notice: Subject to any disclaimer, the term of this patent is extended or adjusted under 35 U.S.C. 154(b) by 0 days.

(21) Appl. No.: 09/448,129

(22) Filed: Nov. 24, 1999

(51) Int. Cl.⁷ .................................................. A61B 8/00

(52) U.S. Cl. ...................................... 600/459; 600/460

(58) Field of Search ................................. 600/459, 437, 600/443, 407, 444, 455

(56) References Cited

U.S. PATENT DOCUMENTS

| | | |
|---|---|---|
| 4,100,916 A | 7/1978 | King |
| 4,849,692 A | 7/1989 | Blood |
| 4,945,305 A | 7/1990 | Blood |
| 5,353,354 A | 10/1994 | Keller et al. |
| 5,585,546 A | 12/1996 | Gururaja et al. |
| 5,787,889 A | 8/1998 | Edwards et al. |
| 5,924,989 A | 7/1999 | Polz |
| 5,924,991 A | 7/1999 | Hossack et al. |
| 5,924,992 A | 7/1999 | Park et al. |
| 5,928,151 A | 7/1999 | Hossack et al. |
| 6,171,248 B1 * | 1/2000 | Hossack et al. ............ 600/459 |
| 6,122,538 A * | 9/2000 | Sliwa, Jr. et al. ........... 600/407 |
| 6,193,657 B1 * | 2/2001 | Drapkin ...................... 600/437 |

OTHER PUBLICATIONS

"Calibration and Validation of Free–hand 3D Ultrasound Systems based on DC Magnetic Tracking," Pagoulatos et al., SPIE Conference on Image Display, San Diego, Ca., SPIE vol. 3335, pp. 59–71, (Feb. 1998).

"Performance of a Miniature Magnetic Position Sensor for Three–Dimensional Ultrasound Imaging," Leotta et al., Ultrasound in Med & Biol., vol. 23, No. 4, pp. 597–609 (1997).

"3D Ultrasonic Image Feature Localization Based on Magnetic Scanhead Tracking: In Vitro Calibration and Validation," Detmer et al., Ultrasound in Med. & Biol., vol. 20, No. 9, pp. 923–936 (1994).

"4D Echo–Scan Operating Manual, Part 1: Data Acquisition, Operating Instructions," TomTec Imaging Systems, A.19.0049/01, pp. 3–17 to 3–24 (1999).

(List continued on next page.)

Primary Examiner—Marvin M. Lateef
Assistant Examiner—Maulin Patel
(74) Attorney, Agent, or Firm—Brinks Hofer Gilson & Lione (57) ABSTRACT

The preferred embodiments described herein provide a medical diagnostic ultrasonic transducer probe and imaging system for use with a position and orientation sensor. In one preferred embodiment, an ultrasonic transducer probe comprises a position and orientation sensor and a memory device comprising calibration data for the position and orientation sensor. The memory device is adapted to provide the calibration data to a medical diagnostic ultrasound imaging system coupled with the ultrasonic transducer probe. In another preferred embodiment, a medical diagnostic ultrasound imaging system comprises a memory device comprising a plurality of position and orientation sensor calibration data. Each of the plurality of position and orientation sensor calibration data is associated with a respective ultrasonic transducer probe family. In operation, identification of a probe family of an ultrasonic transducer probe is provided to the ultrasound system. The ultrasound system then selects the position and orientation sensor calibration data corresponding to the identified probe family.

31 Claims, 5 Drawing Sheets

OTHER PUBLICATIONS

"3D–Freescan—The solution for 3D ultrasound," Echotech, 4 pages (undated).

Installation and Operation Guide for Flock of Birds Systems, Ascension Technology Corp., pp. 69–73, (undated).

* cited by examiner

MEDICAL DIAGNOSTIC ULTRASONIC TRANSDUCER PROBE AND IMAGING SYSTEM FOR USE WITH A POSITION AND ORIENTATION SENSOR

BACKGROUND

A position and orientation sensor, such as a magnetic position and orientation sensor, can be attached to a transducer probe to determine the position and orientation of the sensor with respect to a transmitter. To correlate the location of the sensor to the location of an image plane produced by the probe, it is often required to calibrate the position and orientation of the sensor with the position and orientation of the image plane. The calibration step can be difficult to perform, especially for sonographers who are unfamiliar with position and orientation sensor technology.

The requirement of calibrating transducer probe/sensor pairs can limit the widespread use of position and orientation sensors with ultrasonic transducer probes. For example, some transducer probe/sensor pairs are calibrated on site by a technician who stores the calibration data on an ultrasound imaging system that is to be used in conjunction with the probe/sensor pair. If a sonographer desires to use the probe with a different ultrasound imaging system, the calibration step typically needs to be repeated with that different ultrasound imaging system. Because many sonographers find the calibration step difficult to perform, in practice, probe/sensor pairs are often used only with a single ultrasound imaging system. As another example, consider position and orientation sensors that are removably attachable to an ultrasonic transducer probe. Although removably attachable sensors can be used with more than one transducer probe, many removably attachable sensors are used only with the probes for which they are initially calibrated since many sonographers are unable or unwilling to calibrate the sensors with different probes.

There is a need, therefore, for a medical diagnostic ultrasonic transducer probe and imaging system for use with a position and orientation sensor that overcomes these difficulties.

SUMMARY

The present invention is defined by the following claims, and nothing in this section should be taken as a limitation on those claims.

By way of introduction, the preferred embodiments described below provide a medical diagnostic ultrasonic transducer probe and imaging system for use with a position and orientation sensor. In one preferred embodiment, an ultrasonic transducer probe comprises a position and orientation sensor and a memory device comprising calibration data for the position and orientation sensor. The memory device is adapted to provide the calibration data to a medical diagnostic ultrasound imaging system coupled with the ultrasonic transducer probe.

In another preferred embodiment, a medical diagnostic ultrasound imaging system comprises a memory device comprising a plurality of position and orientation sensor calibration data. Each of the plurality of position and orientation sensor calibration data is associated with a respective ultrasonic transducer probe family. In operation, identification of a probe family of an ultrasonic transducer probe is provided to the ultrasound system. The ultrasound system then selects the position and orientation sensor calibration data corresponding to the identified probe family.

The preferred embodiments will now be described with reference to the attached drawings.

DETAILED DESCRIPTION OF THE PRESENTLY PREFERRED EMBODIMENTS

Brief Overview of Position and Orientation Sensors

Figure 1:
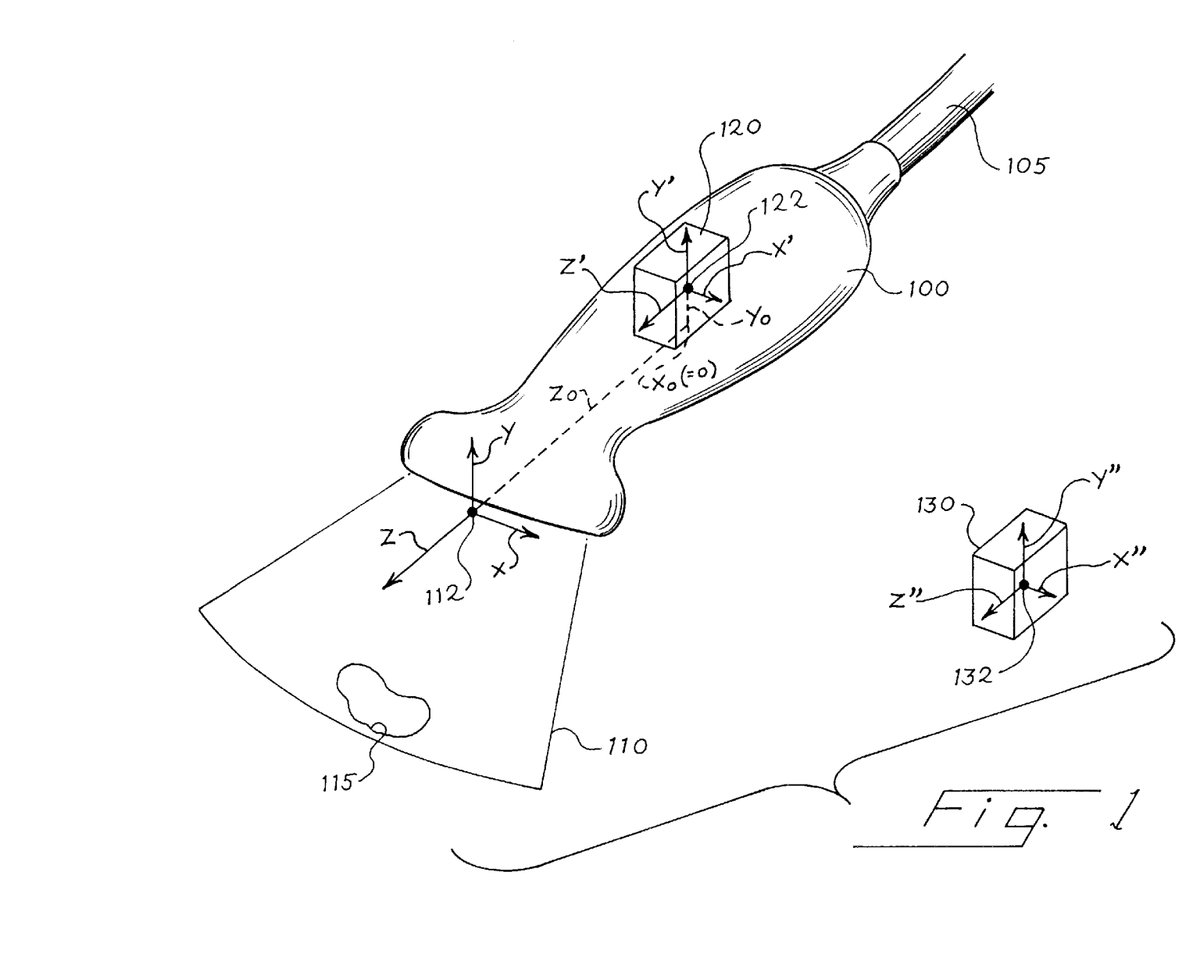
FIG. 1 is an illustration of an ultrasonic transducer probe of a presently preferred embodiment.

Turning now to the drawings, FIG. 1 is an illustration of an ultrasonic transducer probe 100 of a presently preferred embodiment. At least one transducer element (not shown) of the ultrasonic transducer probe 100 generates an image plane 110, which in FIG. 1 is being used to scan a region of interest 115. The ultrasonic transducer probe 100 has a position and orientation sensor 120 attached to the housing of the probe 100 to determine the position and orientation of the image plane 110. A medical diagnostic ultrasound imaging system (not shown) coupled with the probe 100 via the probe cable 105 can use the data generated by the sensor 120 to determine the position and orientation of the sensor 120 and/or the image plane 110, as described below.

In this preferred embodiment, the position and orientation sensor 120 is a magnetic sensor that monitors the free-hand movement of the transducer probe 100 in six degrees of freedom with respect to a transmitter 130. As shown in FIG. 1, the position and orientation sensor 120 and the transmitter 130 each define an origin (122, 132, respectively) defined by three orthogonal axes (X', Y', Z' and X", Y", Z", respectively). The sensor 120 monitors the translation of the origin 122 with respect to the origin 132 of the transmitter 130 to determine position and monitors the rotation of the X', Y', Z' axes with respect to the X", Y", Z" axes of the transmitter 130 to determine orientation.

The position and orientation of the sensor 120 can be used to determine the position and orientation of the image plane 110. As shown in FIG. 1, the image plane 110 defines an origin 112 defined by three orthogonal axes X, Y, Z, which are preferably aligned with the origin of a center acoustic line generated by the transducer probe 100. The position of the origin 122 and the orientation of axes X',Y',Z' of the position and orientation sensor 120 may not precisely coincide with the position of the origin 112 and the orientation of the axes X,Y,Z of the image plane 110. For example, in FIG. 1, the origin 112 of the image plane 110 is offset from the origin 122 of the position and orientation sensor 120 by a distance $Z_0$ along the Z-direction and a distance of $Y_0$ along the Y-direction. (In FIG. 1, there is no offset along the X-direction nor is there a rotational offset in the orientation of the axes.) Accordingly, the position and orientation of the sensor 120 does not directly describe the position and orientation of the image plane 110.

To determine the position and orientation of the image plane 110 from the position and orientation of the sensor 120, position and orientation sensor calibration data is used to transform the position and orientation of the sensor 120 to the position and orientation of the image plane 110. For simplicity, the term "position and orientation" is used to broadly refer to position and/or orientation. Accordingly, if the sensor has the same orientation as the image plane, the position and orientation calibration data may not contain any orientation calibration data. Similarly, as shown in FIG. 1, a sensor may not have an positional offset with respect to one or more axes of the image plane.

There are a number of ways of defining the image plane/sensor offset. One method of calibrating at least some types of sensors uses three orthogonal linear dimension offsets in X, Y, Z and three rotation angles about each these axes. Other methods include using a position transformation matrix or quaternions, which are described in the user manual for the mini Bird™ and the Flock of Birds™ systems by Ascension Technology Corp. (Burlington, Vt.). Other examples of techniques that can be used to generate calibration data for some types of position and orientation sensors are described in the following (all of which are hereby incorporated by reference): "Calibration and Validation of Free-hand 3D Ultrasound Systems based on DC Magnetic Tracking," Pagoulatos et al., SPIE Conference on Image Display, San Diego, Ca., SPIE Vol. 3335, pp. 59–71 (Feb. 1998); "Performance of a Miniature Magnetic Position Sensor for Three-Dimensional Ultrasound Imaging," Leotta et al., Ultrasound in Med. & Biol., Vol. 23, No. 4, pp. 597–609 (1997); and "3D Ultrasonic Image Feature Localization Based on Magnetic Scanhead Tracking: In Vitro Calibration and Validation," Detmer et al., Ultrasound in Med. & Biol., Vol. 20, No. 9, pp. 923–936 (1994)(which discusses a technique for determining the offsets of a magnetic sensor from an acoustic beam axis).

Ultrasonic Transducer Probe with Encoded Calibration Data Embodiments

As described above, ultrasound transducer probes with position and orientation sensors are typically used only with ultrasound systems that contain the calibration data for the probe/sensor pair. Conventionally, a probe/sensor pair is calibrated, and the calibration data is stored in the ultrasound imaging system that will be used in conjunction with the probe/sensor pair. If the probe/sensor pair is to be used with a different ultrasound system, the probe/sensor pair typically needs to be re-calibrated on that different ultrasound system. Because sonographers are often unable or unwilling to perform probe/sensor pair calibration, probe/sensor pairs are often used only with the ultrasound system for which the pair was initially calibrated.

Figure 2:
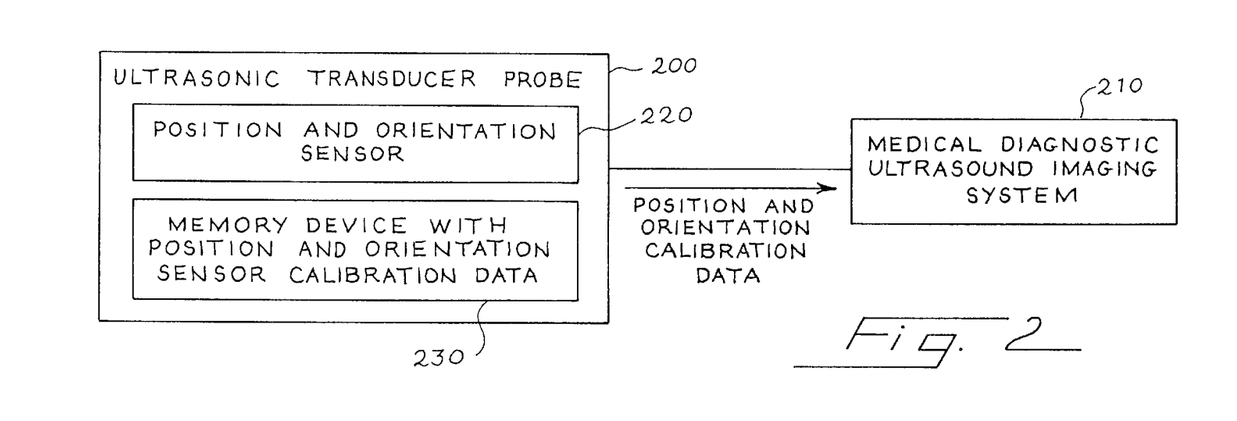
FIG. 2 is a block diagram of an ultrasonic transducer probe and a medical diagnostic ultrasound imaging system of another presently preferred embodiment.

To increase probe portability, the ultrasonic transducer probe 200 of FIG. 2 comprises a position and orientation sensor 220 and a memory device 230 storing calibration data for the position and orientation sensor 220. For simplicity, the term "memory device" is intended to broadly refer to any suitable data storage device, which, in this preferred embodiment, can store calibration data for the position and orientation sensor 220. For example, the memory device can be a permanent memory device (such as a permanent integrated circuit or PROM whose data is permanently resident in the device) or a volatile memory device (such as RAM whose data is loaded from another device, such as a hard disk or tape). It is preferred that the memory device 230 be a memory integrated circuit, such as an EPROM (see U.S. Pat. No. 5,585,546) located in the connector of the probe cable. It should be noted that the memory device can be located in any suitable location in or on the probe (e.g., in the probe connector or in the probe housing).

In operation, when the probe 200 is coupled with a medical diagnostic ultrasound imaging system (such as system 210 of FIG. 2), the calibration data for the position and orientation sensor 220 is transferred to the system 210. The calibration data can be automatically sent to the ultrasound system 210, or a component of the ultrasound system 210 (such as a processor) can read the calibration data from the memory device 230.

Since the calibration data for the probe 200 is stored in the memory device 230 of the probe 200, the calibration data is transported with the probe 200. Accordingly, unlike prior probes which are limited in use with a specific ultrasound imaging system, the transducer probe 200 of this preferred embodiment can be immediately coupled with any compatible ultrasound imaging system without re-calibrating the probe/sensor pair.

In one preferred embodiment, the calibration data stored in the memory device 230 is generated by first attaching the sensor 220 to the probe 200 and then performing a calibration step. For example, the probe 200 can first be manufactured and equipped with the sensor 200 at the transducer factory and then calibrated, with the calibration data subsequently stored in the memory device 230. In another preferred embodiment, instead of calibrating the probe/sensor pair after the sensor is attached, the probe 200 can be manufactured with locating features that allow the sensor 220 to be attached to the probe 200 at a predetermined location, which is correlated with predetermined calibration data stored in the memory device 230. With this preferred embodiment, which is described in more detail below, the manufactured transducer probe will not require position and orientation sensor calibration on a per transducer probe basis. Instead, a single prototype probe with locating features can be calibrated, and subsequent transducer probes can be manufactured in accordance with the calibrated prototype probe.

As also described below, the position and orientation sensor 220 can be integral with, permanently attachable to, or removably attachable to the transducer probe 200.

Ultrasound Imaging System with Probe Family Calibration Data Embodiments

Figure 3:
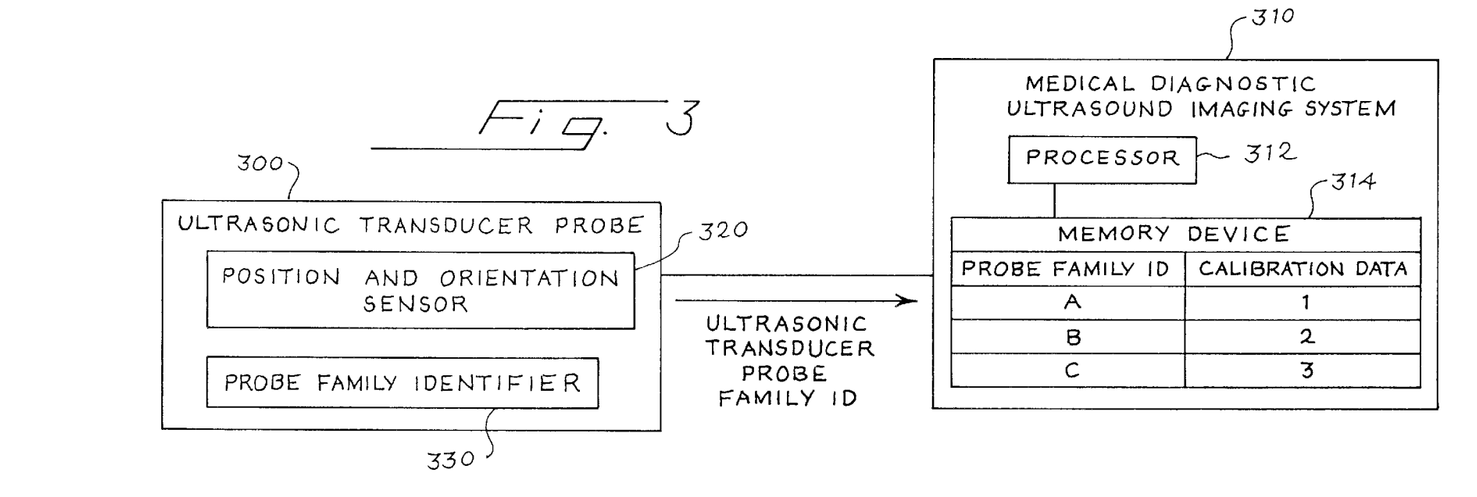
FIG. 3 is a block diagram of an ultrasonic transducer probe and a medical diagnostic ultrasound imaging system of another presently preferred embodiment.

Turning again to the drawings, FIG. 3 is a block diagram of medical diagnostic ultrasound imaging system 310 of another presently preferred embodiment. As shown in FIG. 3, the ultrasound system 310 comprises a processor 312 and a memory device 314. As described above, a memory device can be a permanent memory device (such as a permanent integrated circuit or PROM whose data is permanently resident in the device), a volatile memory device (such as RAM whose data is loaded from another device, such as a hard disk or tape), or any other suitable data storage device, which, in this preferred embodiment, can store a plurality of position and orientation sensor calibration data associated with respective ultrasonic transducer probe families. The processor 312 and/or memory device 314 can each be separate from or combined with (in part or in whole) other processors and/or memory devices, respectively, of the ultrasound system 310, which are not shown for simplicity. In this preferred embodiment, the memory device 314 comprises a plurality of position and orientation sensor calibration data (data sets 1, 2, and 3), each associated with a respective ultrasonic transducer probe family (probe families A, B, and C). As used herein, the term "ultrasonic transducer probe family" refers to a set of two or more ultrasonic transducer probes.

In operation, the identification of an ultrasonic transducer probe family of an ultrasonic transducer probe is provided to the ultrasound system 310. For example, a user of the ultrasonic transducer probe can manually provide the ultrasound system 310 with the ultrasonic transducer probe family identification (e.g., via a keyboard of the ultrasound system 310). It is preferred, however, that the ultrasonic transducer probe have a probe family identifier 330, which provides the ultrasound system 310 with the family identification of the probe. For simplicity, the term "probe family identifier" is intended to broadly refer to any identifier that can passively or actively provide a probe's family identification to an ultrasound system. The "probe family identifier" can be located in any suitable location in or on the probe (e.g., in or on the probe connector, the probe cable, the cable strain relief, or the probe housing).

It is preferred that the probe family identifier be a binary pin code in the connector of the ultrasound probe cable. For example, a set of eight pins in the probe's connector can either be electronically open or grounded, indicating binary 1 or 0. When the probe connector is plugged into the ultrasound system the ultrasound system can determine the probe family based on the binary open circuit/ground configuration of the pins. A probe family identifier can also be a memory device such as a permanent memory device (e.g., a permanent integrated circuit or PROM whose data is permanently resident in the device), a volatile memory device (e.g., RAM whose data is loaded from another device, such as a hard disk or tape), or a memory integrated circuit, such as an EPROM (see U.S. Pat. No. 5,585,546). The probe family identifier can also take the form of a non-electronic device. For example, the probe family identifier can take the form of a bar code printed on the probe housing. In operation, a bar code reader coupled with the ultrasound system reads the bar code printed on the probe housing, and the ultrasound system determines which probe family is identified by the bar code.

When the transducer probe family identification is provided to the ultrasound system 310, the processor 312 uses the probe family identification information to select the calibration data corresponding to the identified transducer probe family type. For example, if a transducer probe from family B is used, the processor 312 selects calibration data set 2 from the memory device 314. Because calibration data is stored on a per family basis, calibration need only be performed once per family instead of once per individual probe of the family. In other words, with this preferred embodiment, calibration can be performed on a per family (e.g., per model type) basis by the manufacturer of the probe instead of on a per probe (e.g., per serial number) basis by a sonographer who may not be able to perform the required calibration. Accordingly, any probe from a family type stored on the ultrasound system can be used without position and orientation calibration, unlike prior systems which require each probe from a family to be calibrated.

To ensure that transducer probes from a transducer probe family can use the same position and orientation calibration data, it is preferred that each probe of a given probe family be manufactured with a position and orientation sensor locating feature in substantially the same location. As used herein, the term "position and orientation sensor locating feature" broadly refers to one or more features that can be used to place a position and orientation sensor in or on an ultrasonic transducer probe at a given location. For example, a locating feature can include, but is not limited to, one or more of the following: recesses, protrusions, graphics, mechanical and/or magnetic locating devices, or any combination thereof A locating feature can be internally or externally located in the probe and can be placed in any suitable area of the probe. Since locating features are formed in substantially the same location on each probe of a family, a position and orientation sensor attached to any probe of a family is associated with the same position and orientation calibration data.

Figure 4:
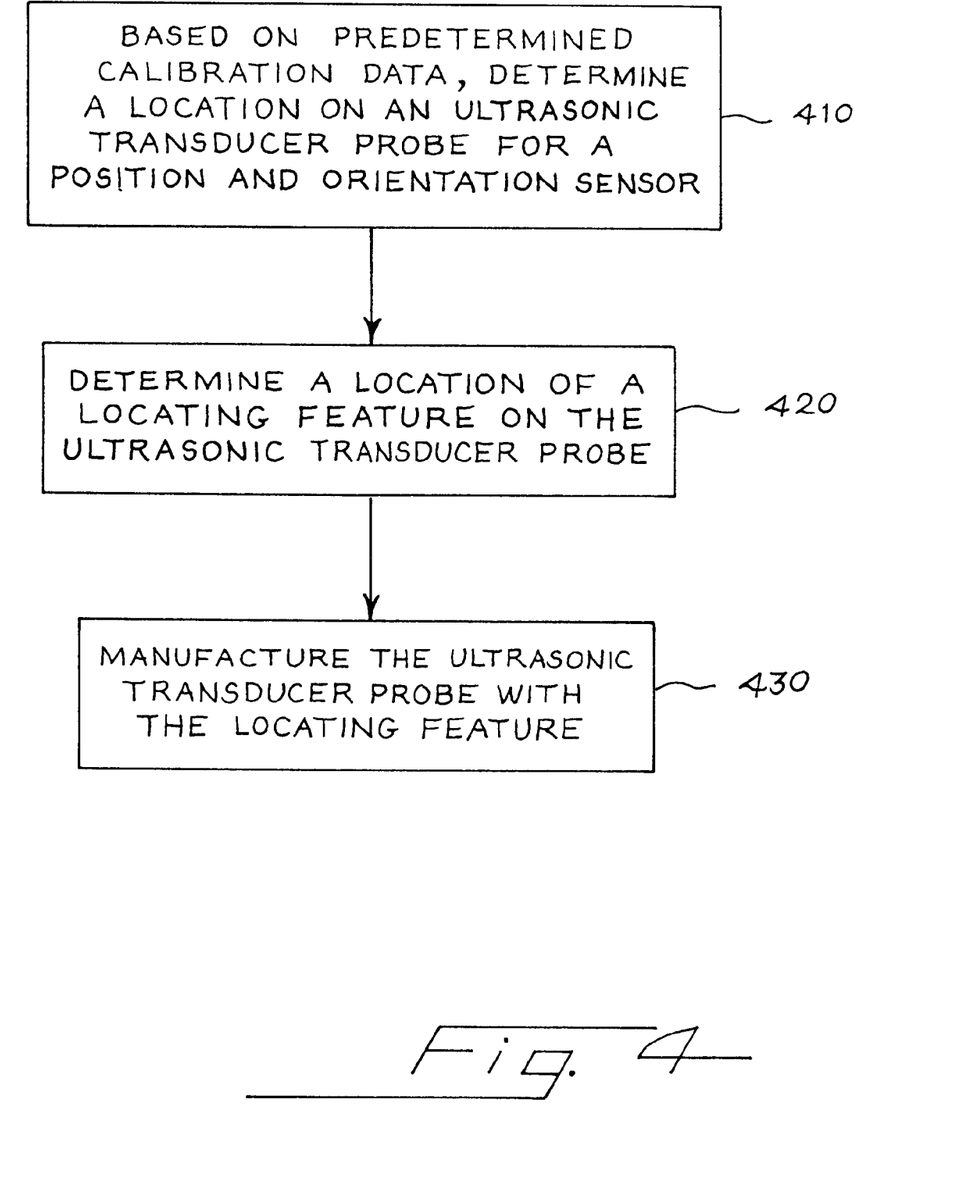
FIG. 4 is a flow chart of a method of manufacturing an ultrasonic transducer probe of another presently preferred embodiment.

FIG. 4 is a flow chart of a preferred method of manufacturing an ultrasonic transducer probe. First, based on predetermined calibration data, a location on an ultrasonic transducer probe for a position and orientation sensor is determined (block 410). The predetermined calibration data can be generated, for example, by building a transducer probe prototype and calibrating the prototype with a position and orientation sensor at a chosen location. Next, a location of a locating feature on the ultrasonic transducer probe is determined (block 420). The locating feature is adapted to locate the position and orientation sensor at the location determined in block 410. For example, the locating feature can be located on the probe to allow a position and location sensor to be located at the same location as the sensor calibrated with the transducer probe prototype. Finally, the ultrasonic transducer probe is manufactured with the locating feature placed at the location determined in block 420 (block 430). By using this preferred method, each probe of a given transducer probe family is manufactured with locating features that allow a position and orientation sensor to be attached to any of the probes in the family at substantially the same location. Accordingly, an ultrasound system that stores calibration data on a probe family basis can be used to avoid the need for subsequent position-and-orientation calibration.

To form the position and orientation sensor locating features with the desired degree of accuracy, it is preferred that a computer numerical control (CNC) machining process or an injection molding process be used to manufacture the ultrasonic transducer probes. True-Tech Corporation (Fremont, Calif.) and Contour Plastics (Baldwin, Wis.) offer suitable CNC machining and injection molding processes, respectively.

To improve accuracy, it is preferred that the position and orientation sensor be placed close to the transducer elements (i.e., to the image plane). Such placement, however, can conflict with user ergonomics. FIGS. 5–8 illustrate various types and locations of locating features of several preferred embodiments, which provide a compromise between sensor accuracy and user ergonomics. In these preferred embodiments, a position and orientation sensor is directly or indirectly (via an adapter) reattachably coupled to a transducer probe. This allows the sensor to be attached/detached from a probe and reattached to the same or different probe. In these preferred embodiments, the sensor can be attached to different probes in the same family without position and orientation calibration. As described below, the sensor can also be integral with or permanently attachable to the transducer probe.

Figure 5:
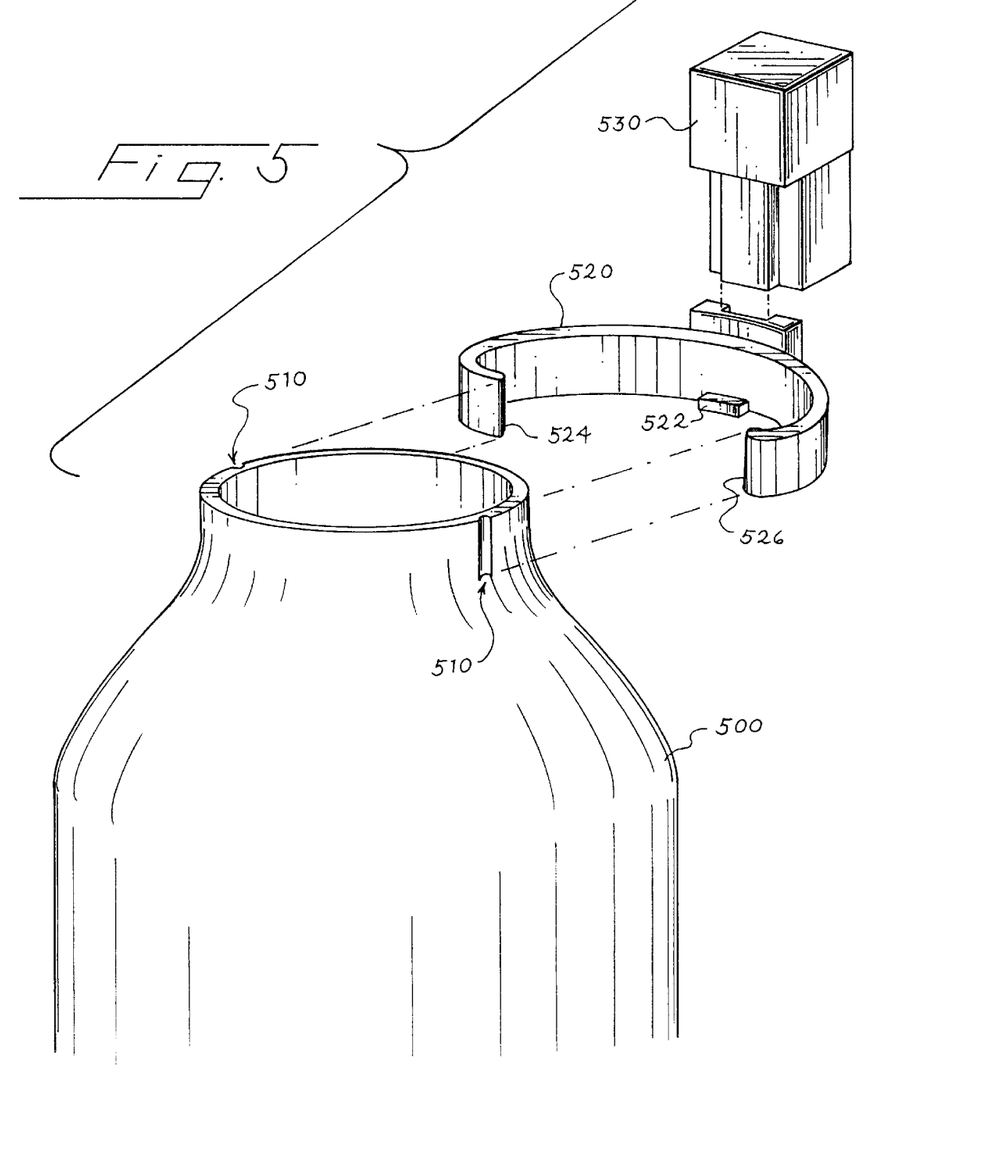
FIG. 5 is an illustration of an ultrasonic transducer probe of another presently preferred embodiment in which position and orientation sensor locating features are formed in a housing portion of the probe.

In the preferred embodiment of FIG. 5, position and orientation sensor locating features 510 are formed in an end of the housing section 500 of an ultrasonic transducer probe proximate to the cable section of the probe (not shown). In this preferred embodiment, the locating features 510 take the form of two grooves longitudinally disposed on opposite sides of the probe housing 500 and a slot (not shown) disposed between the two grooves. These locating features fit corresponding locating details (locating tab 522 and clips 524, 526) of an adapter 520 that releasably holds a position and orientation sensor 530. It is preferred that the adapter 520 be made from a material that is strong enough to ensure sturdy and accurate attachment of the position sensor 530 to the probe housing 500 while allowing the adapter 520 to be snapped on to and off of the probe housing 500. It should be noted that in this and other preferred embodiments, a single adapter or multiple adapters fitted with each other can be used. For example, a first adapter can be fitted to the transducer probe, and a second adapter, which attaches to the first adapter, can be fitted to the position and orientation sensor. When multiple adapters are used, it is preferred to minimize their total number to reduce compound errors. It is preferred that the adapter and the probe housing be made of the material sold under the trade name Radel® by Amaco Performance Products (Alpharetta, Georgia).

Figure 6:
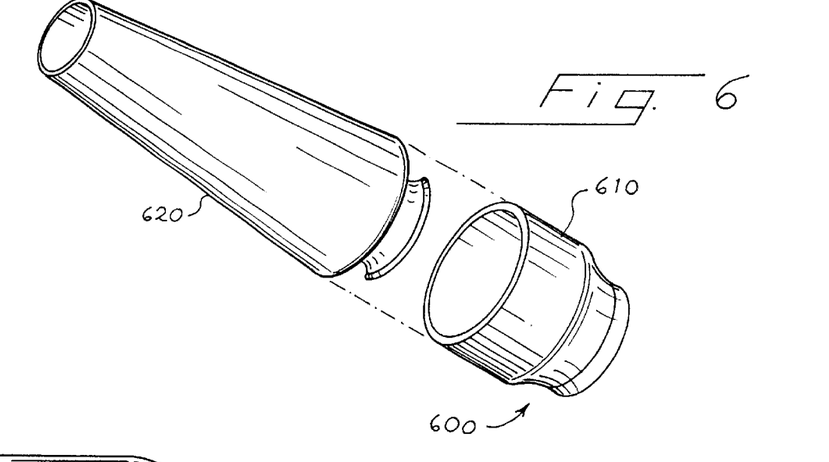
FIG. 6 is an illustration of an ultrasonic transducer probe of another presently preferred embodiment in which position and orientation sensor locating features are formed in an insert located between a housing portion and a cable portion of the probe.
Figure 7:
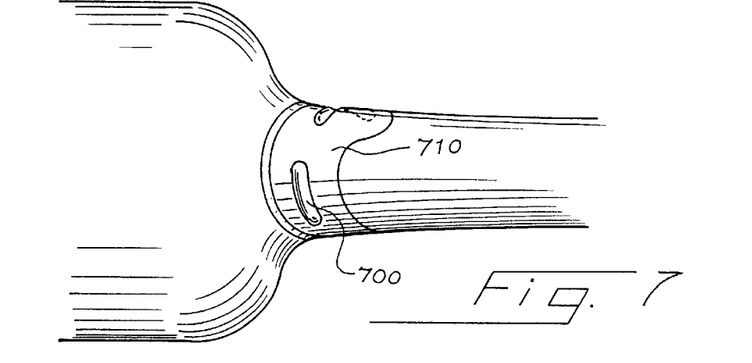
FIG. 7 is an illustration of an ultrasonic transducer probe of another presently preferred embodiment in which position and orientation sensor locating features are formed in a cable portion of the probe.
Figure 8:
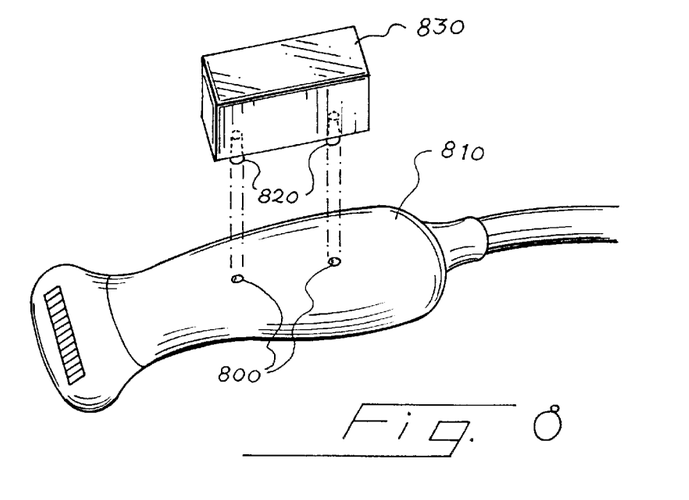
FIG. 8 is an illustration of an ultrasonic transducer probe of another presently preferred embodiment in which position and orientation sensor locating features are formed in a housing portion of the probe.

In the preferred embodiment shown in FIG. 6, the locating features 600 are formed as machined indentations in an insert 610 located between the strain relief 620 of the probe cable and the probe housing (not shown), while in FIG. 7, the locating features 700 are formed in the strain relief 710 itself As with the preferred embodiment shown in FIG. 5, the locating features of the preferred embodiments shown in FIGS. 6 and 7 are formed to fit corresponding locating details on an adapter that holds a position and orientation sensor. In another preferred embodiment, shown in FIG. 8, the locating features 800 (two matching machined holes) on the probe housing 810 are formed to fit locating details 820 (two split pin locating studs) on the position and orientation sensor 830. With this preferred embodiment, the position and orientation sensor 830 is directly attached to the probe housing 810 without the use of an adapter.

It is important to note that any of the various aspects of any of the preferred embodiments can be used alone or in combination. For example, an ultrasonic probe can be from a probe family with commonly-located position and orientation sensor location features and can also be provided with a memory device storing calibration data for that specific probe. It is also important to note that any of the preferred embodiments described above can be used with any suitable transducer type (e.g., 1D transducers, 1.5D transducers, plano-concave transducers, etc.) and with any suitable imaging mode (e.g., B-mode imaging, Doppler imaging, tissue harmonic imaging, contrast agent harmonic imaging, etc.). Although a single transducer element can be used, it is preferred that a phased-array, piezoelectric-based transducer be used.

It is preferred that the ultrasound system perform the embodiments described above using any appropriate software and/or hardware components. It should be understood that any appropriate hardware, analog or digital, and any appropriate software language can be used. Additionally, the embodiments described above can be implemented exclusively with hardware. It should also be understood that the term "ultrasound imaging system" refers to an ultrasound imaging system with or without an attendant processor, such as a computer for processing three-dimensional imaging information. For example, the ultrasound system can have an auxiliary, PC-based computer whose memory contains the calibration data. The PC can be in or on the ultrasound system and can be fully or partially integrated with the ultrasound system. See U.S. patent application Ser. No. 09/196,207, which is hereby incorporated by reference. For example, the ultrasound system can read pin code information from the transducer probe and transfer the information to the PC. The PC can then look up the relevant calibration data from a look up table using the transducer probe identification information.

It should be noted that the preferred embodiments described above can be used in any suitable application. For example, the preferred embodiments can be used in conjunction with three dimensional reconstruction and display of ultrasound images. The transducer probes and sensors described above can be used to acquire multiple two-dimensional ultrasound images with position and orientation data. These images and data can then be used to form and display a three-dimensional reconstruction. See U.S. Pat. No. 5,928,151, which is hereby incorporated by reference.

Further, with any of the preferred embodiments described above, the position and orientation sensor can be integral with the probe, permanently attachable to the probe, or removably attachable and reattachable to the probe. Preferably, the position and orientation sensor takes the form of a magnetic position and orientation sensor. Suitable magnetic sensors are described in U.S. Pat. Nos. 4,945,305 and 4,849,692 to Blood. It is preferred that magnetic position and orientation sensors from Ascension Technology Corp (Burlington, Vt.) be used (such as the mini Bird™ and the Flock of Birds™ systems). Alternatively, the 3 Space Fastrak from Polhemus (Colchester, Vt.) can be used. Additionally, non-magnetic position and orientation sensors can be used. For example, a spaced arrangement of LEDs, such as infra-red LEDs, on the transducer can be activated in sequence and monitored with a camera. The position and orientation can then be inferred from an image of the LEDs generated by the camera. One such device is manufactured by Surgical Navigation Technologies of Broomfield, Colo. Other optical sensors can be used, such as the Flashpoint 5000 3D Localizer from Image Guided Technologies (Denver, Colo.). Position and orientation data can also be generated by accelerometers (see U.S. Pat. No. 5,353,354 to Keller) or acoustic sensors (see U.S. Pat. No. 4,100,916 to King, which determines position information from the time of flight of acoustic impulses generated by a source (typically a spark plug) on the transducer to a spaced arrangement of microphones).

It is intended that the foregoing detailed description be understood as an illustration of selected forms that the invention can take and not as a definition of the invention. It is only the following claims, including all equivalents, that are intended to define the scope of this invention.

What is claimed is:

1. For use with a medical diagnostic ultrasound imaging system, an ultrasonic transducer probe comprising:
   a position and orientation sensor; and
   a memory device comprising calibration data for the position and orientation sensor, wherein the memory device is adapted to provide the calibration data to a medical diagnostic ultrasound imaging system coupled with the ultrasonic transducer probe.

2. In a medical diagnostic ultrasound imaging system coupled with an ultrasonic transducer probe comprising a position and orientation sensor, a method of providing position and orientation sensor calibration data to the medical diagnostic ultrasound imaging system, the method comprising:
   (a) providing an ultrasonic transducer probe comprising a position and orientation sensor and a memory device comprising calibration data for the position and orientation sensor;

(b) coupling the ultrasonic transducer probe with a medical diagnostic ultrasound imaging system; and (c) providing the calibration data to the medical diagnostic ultrasound imaging system from the memory device of the ultrasonic transducer probe.

3. A medical diagnostic ultrasound imaging system comprising:

a memory device comprising a plurality of position and orientation sensor calibration data, each of said plurality of position and orientation sensor calibration data being associated with a respective ultrasonic transducer probe family; and an ultrasonic transducer probe associated with an ultrasonic transducer probe family, the ultrasonic transducer probe comprising:

a position and orientation sensor; and a probe family identifier identifying the ultrasonic transducer probe family;

wherein the medical diagnostic ultrasound imaging system selects the position and orientation sensor calibration data corresponding to the ultrasonic transducer probe family identified by the probe family identifier.

4. In a medical diagnostic ultrasound imaging system coupled with an ultrasonic transducer probe comprising a position and orientation sensor, a method of selecting position and orientation sensor calibration data, the method comprising:

(a) providing a medical diagnostic ultrasound imaging system comprising a memory device comprising a plurality of position and orientation sensor calibration data, each of said plurality of position and orientation sensor calibration data being associated with a respective ultrasonic transducer probe family;

(b) providing the medical diagnostic ultrasound imaging system with an identification of an ultrasonic transducer probe family of an ultrasonic transducer probe coupled with the medical diagnostic ultrasound imaging system; and (c) selecting the position and orientation calibration data associated with the ultrasonic transducer probe family of the ultrasonic transducer probe.

5. The invention of claim 4, wherein the ultrasonic transducer probe comprises a probe family identifier identifying the ultrasonic transducer probe family, and wherein the identification of the ultrasonic transducer probe family is provided to the medical diagnostic ultrasound imaging system from the probe family identifier of the ultrasonic transducer probe.

6. The invention of claim 4, wherein a user of the ultrasonic transducer probe manually provides the medical diagnostic ultrasound imaging system with the identification of the ultrasonic transducer probe family.

7. The invention of claim 3 or 4, wherein the ultrasonic transducer probe family comprises two or more ultrasonic transducer probes that have substantially the same position and orientation sensor calibration data.

8. The invention of claim 3 or 4, wherein the ultrasonic transducer probe family comprises two or more ultrasonic transducer probes, each comprising a position and orientation sensor locating feature located in substantially the same location on each of said two or more ultrasonic transducer probes.

9. The invention of claim 1, 2, 3, or 4, wherein the position and orientation sensor calibration data correlates an origin of the position and orientation sensor with an origin of a center acoustic line generated by the ultrasonic transducer probe.

10. The invention of claim 1, 2, 3, or 4, wherein the position and orientation sensor is selected from the group consisting of a magnetic sensor, an optical sensor, an accelerometer, and an acoustic sensor.

11. The invention of claim 1, 2, 3, or 4, wherein the position and orientation sensor is removably attachable to the ultrasonic transducer probe and is reattachable without subsequent position-and-orientation calibration.

12. A method for manufacturing an ultrasonic transducer probe adapted for use with a medical diagnostic ultrasound imaging system, the method comprising:

(a) based on predetermined position and orientation sensor calibration data, determining a location on an ultrasonic transducer probe for a position and orientation sensor;

(b) determining a location of a locating feature on the ultrasonic transducer probe, the locating feature adapted to locate the position and orientation sensor at the location determined in (a); and (c) manufacturing the ultrasonic transducer probe with the locating feature at the location determined in (b);

whereby the locating feature allows the position and orientation sensor to be attached to the ultrasonic transducer probe without subsequent position-and-orientation calibration.

13. The invention of claim 12, wherein the ultrasonic transducer probe is manufactured in (c) using an injection molding process.

14. The invention of claim 12, wherein the ultrasonic transducer probe is manufactured in (c) using a computer numerical control (CNC) machining process.

15. The invention of claim 12, wherein the ultrasonic transducer probe comprises a housing portion and a cable portion, and wherein the locating feature is formed in an insert located between the housing portion and the cable portion.

16. The invention of claim 12, wherein the ultrasonic transducer probe comprises a housing portion and a cable portion, and wherein the locating feature is formed in the housing portion proximate to the cable portion.

17. The invention of claim 12, wherein the ultrasonic transducer probe comprises a housing portion and a cable portion, and wherein the locating feature is formed in the cable portion proximate to the housing portion.

18. The invention of claim 17, wherein the cable portion comprises a strain relief portion, and wherein the locating feature is formed in the strain relief portion.

19. The invention of claim 12, wherein the locating feature is adapted to allow the position and orientation sensor to be repeatably attached to the ultrasonic transducer probe.

20. The invention of claim 12, wherein the predetermined position and orientation sensor calibration data is determined by calibrating a transducer prototype.

21. The invention of claim 12, wherein the ultrasonic transducer probe is associated with an ultrasonic transducer probe family and wherein the method further comprises providing the ultrasonic transducer probe with a probe family identifier identifying the ultrasonic transducer probe family associated with the ultrasonic transducer probe.

22. The invention of claim 12 further comprising providing the ultrasonic transducer probe with a memory device comprising the predetermined position and orientation sensor calibration data.

23. The invention of claim 1, 2, 3, or 4, wherein the position and orientation sensor is directly attached to the ultrasonic transducer probe.

24. The invention of claim 1, 2, 3, or 4, wherein the position and orientation sensor is attached to the ultrasonic transducer probe with at least one adapter.

25. The invention of claim 3 or 4, wherein the medical diagnostic ultrasound imaging system comprises an auxiliary computer, and wherein the auxiliary computer comprises the memory device comprising the plurality of position and orientation sensor calibration data.

26. The invention of claim 2 or 4 further comprising:
   (d) acquiring, with the ultrasonic transducer probe and position and orientation sensor, a plurality of two-dimensional ultrasound images with position and orientation data; and
   (e) forming a three-dimensional reconstruction of said plurality of two-dimensional ultrasound images.

27. The invention of claim 3, wherein the probe family identifier comprises a second memory device.

28. The invention of claim 3, wherein the probe family identifier comprises a bar code.

29. The invention of claim 3, wherein the probe family identifier comprises a binary pin code.

30. The invention of claim 3, wherein the probe family identifier comprises a permanent memory device.

31. The invention of claim 3, wherein the probe family identifier comprises a volatile memory device.

* * * * *